(12) United States Patent
Takeuchi et al.

(10) Patent No.: US 9,090,714 B2
(45) Date of Patent: Jul. 28, 2015

(54) METHOD OF MAKING HYDROXYALKYLCELLULOSE MICROPARTICLES

(71) Applicant: Nippon Soda Co., Ltd., Tokyo (JP)

(72) Inventors: Hirofumi Takeuchi, Gifu (JP); Satoru Abe, Joetsu (JP); Takeshi Shimotori, Myoko (JP); Gentaro Nemoto, Yamato (JP)

(73) Assignees: Nippon Soda Co., Ltd., Tokyo (JP); Hirofumi Takeuchi, Gifu (JP)

( * ) Notice: Subject to any disclaimer, the term of this patent is extended or adjusted under 35 U.S.C. 154(b) by 0 days.

(21) Appl. No.: 14/021,995

(22) Filed: Sep. 9, 2013

(65) Prior Publication Data

US 2014/0034760 A1 Feb. 6, 2014

Related U.S. Application Data

(62) Division of application No. 13/510,096, filed as application No. PCT/JP2010/070867 on Nov. 24, 2010, now Pat. No. 8,568,787.

(30) Foreign Application Priority Data

Nov. 24, 2009 (JP) ................................. 2009-266821
Jun. 14, 2010 (JP) ................................. 2010-135622

(51) Int. Cl.
*A61K 9/127* (2006.01)
*C08B 15/02* (2006.01)
(Continued)

(52) U.S. Cl.
CPC ............... *C08B 15/02* (2013.01); *A61K 9/0056* (2013.01); *A61K 9/1652* (2013.01); *A61K 9/2054* (2013.01); *C08B 11/08* (2013.01);
(Continued)

(58) Field of Classification Search
CPC .................................................... A61K 9/1652
See application file for complete search history.

(56) References Cited

U.S. PATENT DOCUMENTS 6,680,069 B1 1/2004 Obara
2009/0275672 A1 11/2009 Honma et al.

FOREIGN PATENT DOCUMENTS

EP 1342733 9/2003
JP 01-152103 6/1989
(Continued)

OTHER PUBLICATIONS

Office Action, dated Feb. 28, 2014, issued for Korean Patent Application No. 10-2012-7012768, 11 sheets (with English translation thereof).
(Continued)

*Primary Examiner* — Carlos Azpuru
(74) *Attorney, Agent, or Firm* — Kenyon & Kenyon, LLP

(57) ABSTRACT

Provided is a method of producing hydroxyalkylcellulose microparticles, the method including generating a pulse shock wave, and supplying a hydroxyalkylcellulose aqueous solution to the pulse shock wave generation region, thereby crushing and drying the hydroxyalkylcellulose aqueous solution. According to the production method, hydroxyalkylcellulose microparticles having a volume-average particle size of at least 0.1 μm but less than 15 μm are obtained. By mixing the hydroxyalkylcellulose microparticles with a principal agent and subjecting the resulting mixture to a tablet compression, a solid preparation having excellent tensile strength and disintegration properties can be obtained.

5 Claims, 10 Drawing Sheets

(51) Int. Cl.
  *A61K 9/16* (2006.01)
  *A61K 9/00* (2006.01)
  *A61K 9/20* (2006.01)
  *C08B 11/08* (2006.01)
  *C08J 3/12* (2006.01)
  *C08L 1/28* (2006.01)

(52) U.S. Cl.
  CPC . *C08J 3/12* (2013.01); *C08L 1/284* (2013.01); *C08J 2301/28* (2013.01); *C08L 2205/18* (2013.01); *Y10T 428/2982* (2015.01)

(56) References Cited

FOREIGN PATENT DOCUMENTS

| JP | 06-033939 | 5/1994 |
|---|---|---|
| JP | 06-199660 | 7/1994 |
| JP | 07-070203 | 3/1995 |
| JP | 08-100001 | 4/1996 |
| JP | 09-143080 | 6/1997 |
| JP | 11-322584 | 11/1999 |
| JP | 2000-212068 | 8/2000 |
| JP | 2001-200001 | 7/2001 |
| JP | 2001-322927 | 11/2001 |
| JP | 2002-207030 | 7/2002 |
| JP | 2006-90571 | 4/2006 |
| JP | 2007-176869 | 7/2007 |
| JP | 2007-211006 | 8/2007 |
| JP | 2008-133258 | 6/2008 |
| KR | 1020010042551 A | 5/2001 |
| WO | 2007/123187 | 11/2007 |
| WO | 2008/120548 A2 | 10/2008 |

OTHER PUBLICATIONS

Office Action, dated Nov. 8, 2013, issued for Chinese Patent Application No. 201080052422.3, 25 sheets (with English translation thereof).

International Search Report issued for PCT/JP2010/070867, dated Dec. 21, 2010, 5 pages (with English translation).

Saka, Ayako, et al., "Funmu Kanso HPC o Ketsugozai to shite Mochiita Chokusetsu Dajo", Seizai to Ryushi Sekkei Symposium Koen Yoshishu, 2006, vol. 23, pp. 183-186 (no English translation).

Yasui, Shin'ichiro, et al., "Nan'yosei Yakubutsu Pranlukast Suiwabutsu no Yokaisei no Kaizen-Pulse Nensho Kanso System o Mochiiru Baai", Dai 22 Kai Seizai to Ryushi Sekkei Symposium Koen Yoshishu, Oct. 21, 2005, pp. 232-235 (no English translation).

Taiwanese Office Action, dated Dec. 17, 2012, issued for Taiwanese Patent Application No. 099140331 with English translation thereof, 13 sheets.

Office Action issued in U.S. Appl. No. 13/510,096, dated Jan. 22, 2013.

Office Action issued in U.S. Appl. No. 13/510,096, dated Mar. 29, 2013.

Kawashima et al., "Changes in Controlled Release Funtions of Pulverized Low Substituted Hydroxypropylcellulose by Wet Granulation", Journal of the Society of Powder Technology, Japan, 1992, vol. 29, No. 6, pp. 456-459. (Machine Translation).

METHOD OF MAKING HYDROXYALKYLCELLULOSE MICROPARTICLES

CROSS-REFERENCE TO RELATED APPLICATIONS

This application is a divisional application of U.S. application Ser. No. 13/510,096, filed on May 16, 2012 now U.S. Pat. No. 8,568,787, which is a national phase application of PCT/JP2010/070867 filed on Nov. 24, 2010 which claims priority under 35 U.S.C. 119 to Japanese Patent Application No. 2010-135622, filed Jun. 14, 2010 and Japanese Patent Application No. 2009-266821, filed Nov. 24, 2009, the contents of which are incorporated herein by reference.

TECHNICAL FIELD

The present invention relates to hydroxyalkylcellulose microparticles, a method of producing the same, and a solid preparation containing the microparticles.

BACKGROUND ART

Direct compression methods and granule compression methods and the like are known examples of methods of producing solid preparations. Direct compression methods have fewer steps than granule compression methods, which require a granulation operation, and are also superior from the viewpoint of validation. However, direct compression methods are more readily affected by the properties of the powder, and therefore appropriate control of the powder properties of the principal agent and any additives, and appropriate selection of the production equipment and process are important factors from the viewpoint of achieving stable tablet production. Compression moldability can be particularly problematic in the direct compression method. If the compression moldability is low, then the tablets obtained upon molding tend to have low hardness and suffer from high friability. As a result, the tablets tend to be prone to damage during packaging and filling steps, and during transport. A binder is typically used to improve the compression moldability. However, there are very few compounds that can be used satisfactorily as a binder that can be used in a dry direct compression method and can generate appropriate bonding strength in a small amount.

Hydroxyalkylcellulose is used as a binder and molding base material for addition to solid preparations such as granules and tablets of medicines, as a binder for producing ceramics, as a coating agent for films, and as a viscosity modifier, dispersant or tackifier.

Hydroxyalkylcellulose is usually supplied in powder form. Spray dry methods have been reported as methods of preparing hydroxypropylcellulose particles. When a spray dry method is used, the particles must be prepared from a dilute solution in order to obtain the target particles, which is problematic from a productivity perspective. Further, Patent Document 1 discloses hydroxypropylcellulose particles having a particle size of 1 to 150 µm for use in a tacky layer for a patch. Further, Patent Document 2 and Patent Document 3 disclose low-substitution degree hydroxypropylcellulose particles for use in solid preparations, the particles having a volume-average particle size measured by a dry laser diffraction method of not more than 25 µm. These hydroxypropylcellulose particles are prepared as fluidized bed granules using a powder obtained from a vibration mill or the like.

DOCUMENTS OF RELATED ART

Patent Documents

[Patent Document 1]
Japanese Unexamined Patent Application, First Publication No. Hei 06-199660
[Patent Document 2]
Japanese Unexamined Patent Application, First Publication No. 2001-200001
[Patent Document 3]
Japanese Unexamined Patent Application, First Publication No. 2001-322927
[Patent Document 4]
Japanese Unexamined Patent Application, First Publication No. 2008-133258
[Patent Document 5]
Japanese Examined Patent Application, Second Publication No. Hei 06-33939
[Patent Document 6]
Japanese Unexamined Patent Application, First Publication No. 2006-90571
[Patent Document 7]
Japanese Unexamined Patent Application, First Publication No. 2002-207030

SUMMARY OF THE INVENTION

Problems to be Solved by the Invention

In these patent documents, although the claims include a comprehensive disclosure that includes hydroxyalkylcellulose microparticles having a volume-average particle size of less than 15 µm, Patent Documents 1 to 3 make no disclosure of a production method for obtaining hydroxyalkylcellulose microparticles of less than 15 µm, and include no disclosure to suggest that hydroxyalkylcellulose microparticles of less than 15 µm were actually able to be produced. The particulate hydroxyalkylcellulose actually produced and used in Patent Document 1 has an average particle size of 70 to 130 µm, and the low-substitution degree hydroxypropylcellulose particles actually produced and used in Patent Document 2 and Patent Document 3 have a volume-average particle size of 15 to 23 µm. Further, based on the fact that other related art documents have indicated that if the average particle size is less than 10 µm, then cohesiveness increases and there is a possibility that the flowability of the particles may deteriorate (for example, see Patent Document 4), no attempts have been made to produce hydroxyalkylcellulose microparticles having an average particle size of less than 10 µm, and then actually use such microparticles in solid preparations and the like. Further, hydroxyalkylcellulose particles obtained using a grinding device such as a mill are almost always angular flake-like or irregular shaped particles.

These types of conventional hydroxyalkylcellulose particles exhibit unsatisfactory compression characteristics during tablet production via the direct compression method, and the tensile strength and disintegration properties of the obtained tablets are not always entirely satisfactory.

Accordingly, an object of an aspect of the present invention is to provide hydroxyalkylcellulose microparticles that are suitable for obtaining a solid preparation having excellent tensile strength and disintegration properties.

Means to Solve the Problems

As a result of intensive investigation aimed at achieving the above object, the inventors of the present invention discovered a method of producing hydroxyalkylcellulose microparticles, the method including generating a pulse shock wave, and supplying a hydroxyalkylcellulose aqueous solution to the pulse shock wave generation region, thereby crushing and drying the hydroxyalkylcellulose aqueous solution. The inventors discovered that this production method enabled hydroxyalkylcellulose microparticles having a volume-average particle size of at least 0.1 μm but less than 15 μm to be obtained with ease. Further, the inventors also discovered that when a solid preparation such as a tablet was produced by a direct compression method using the hydroxyalkylcellulose microparticles obtained from this production method, the tensile strength of the solid preparation was enhanced, and the fluctuation in the disintegration properties caused by fluctuations in the compression pressure was extremely small. As a result of further investigation based on these findings, the inventors were able to complete the present invention.

In other words, the method of producing hydroxyalkylcellulose microparticles according to the present invention includes the aspects described below.

<1> A method of producing hydroxyalkylcellulose microparticles, the method including generating a pulse shock wave, and supplying a hydroxyalkylcellulose aqueous solution to the pulse shock wave generation region, thereby crushing and drying the hydroxyalkylcellulose aqueous solution.

<2> The method of producing hydroxyalkylcellulose microparticles according to <1> above, wherein the concentration of the hydroxyalkylcellulose aqueous solution is within a range from 1 to 5% by weight.

<3> The method of producing hydroxyalkylcellulose microparticles according to <1> or <2> above, wherein the shape of the obtained hydroxyalkylcellulose microparticles is spherical.

<4> The method of producing hydroxyalkylcellulose microparticles according to any one of <1> to <3> above, wherein the hydroxyalkylcellulose supplied as an aqueous solution has a viscosity at 20° C. for a 2% aqueous solution that is within a range from 2.0 to 20.0 mPa·s.

<5> The method of producing hydroxyalkylcellulose microparticles according to any one of <1> to <4> above, wherein the hydroxyalkylcellulose supplied as an aqueous solution has a hydroxyalkyl group content within a range from 40 to 80% by weight.

<6> The method of producing hydroxyalkylcellulose microparticles according to any one of <1> to <5> above, wherein the hydroxyalkylcellulose supplied as an aqueous solution is a hydroxypropylcellulose.

<7> A method of producing hydroxyalkylcellulose microparticles, the method including supplying a hydroxyalkylcellulose aqueous solution as a raw material to a crushing and drying apparatus, the crushing and drying apparatus containing a pulse combustor, a raw material supply port positioned close to the outlet of an exhaust pipe of the pulse combustor, and a gas regulation device which sets alterably the particle Reynolds number of an exhaust gas from the pulse combustor that surrounds particles of the supplied raw material to apply continuously generated nonlinear waves to the raw material, thereby crushing and drying the raw material.

<8> The method of producing hydroxyalkylcellulose microparticles according to <7> above, wherein the temperature of the exhaust gas is within a range from 70 to 90° C.

<9> The method of producing hydroxyalkylcellulose microparticles according to <7> or <8> above, wherein the concentration of the hydroxyalkylcellulose aqueous solution is within a range from 1 to 5% by weight.

<10> The method of producing hydroxyalkylcellulose microparticles according to any one of <7> to <9> above, wherein the shape of the obtained hydroxyalkylcellulose microparticles is spherical.

<11> The method of producing hydroxyalkylcellulose microparticles according to any one of <7> to <10> above, wherein the hydroxyalkylcellulose supplied as an aqueous solution has a viscosity at 20° C. for a 2% aqueous solution that is within a range from 2.0 to 20.0 mPa·s.

<12> The method of producing hydroxyalkylcellulose microparticles according to any one of <7> to <11> above, wherein the hydroxyalkylcellulose supplied as an aqueous solution has a hydroxyalkyl group content within a range from 40 to 80% by weight.

<13> The method of producing hydroxyalkylcellulose microparticles according to any one of <7> to <12> above, wherein the hydroxyalkylcellulose supplied as an aqueous solution is a hydroxypropylcellulose.

The hydroxyalkylcellulose microparticles according to the present invention include the aspects described below.

<14> Hydroxyalkylcellulose microparticles obtained using the method according to any one of <1> to <6> above.

<15> Hydroxyalkylcellulose microparticles obtained using the method according to any one of <7> to <13> above.

<16> Hydroxyalkylcellulose microparticles, having a volume-average particle size of at least 0.1 μm but less than 15 μm.

<17> The hydroxyalkylcellulose microparticles according to <16> above, wherein the volume-average particle size is at least 0.1 μm but less than 10 μm.

<18> The hydroxyalkylcellulose microparticles according to <16> or <17> above, wherein the shape of the microparticles is spherical.

<19> The hydroxyalkylcellulose microparticles according to any one of <16> to <18> above, wherein a 2% aqueous solution of the hydroxyalkylcellulose microparticles has a viscosity at 20° C. within a range from 2.0 to 20.0 mPa·s.

<20> The hydroxyalkylcellulose microparticles according to any one of <16> to <18> above, wherein a 2% aqueous solution of the hydroxyalkylcellulose microparticles has a viscosity at 20° C. within a range from 2.0 to 10.0 mPa·s.

<21> The hydroxyalkylcellulose microparticles according to any one of <16> to <20> above, wherein the hydroxyalkyl group content is within a range from 40 to 80% by weight.

<22> The hydroxyalkylcellulose microparticles according to any one of <16> to <21> above, wherein the hydroxyalkylcellulose is a hydroxypropylcellulose.

<23> The hydroxyalkylcellulose microparticles according to any one of <14> to <22> above, wherein the hydroxyalkylcellulose microparticles are used in a solid preparation.

The present invention also includes the aspects described below.

<24> A solid preparation, containing the hydroxyalkylcellulose microparticles of any one of <14> to <22> above.

<25> An orally disintegratable tablet, containing the hydroxyalkylcellulose microparticles of any one of <14> to <22> above.

<26> A method of producing a solid preparation, the method including mixing a principal agent with the hydroxyalkylcellulose microparticles of any one of <14> to <22> to obtain a mixture, and subjecting the mixture to a tablet compression.

Effect of the Invention

According to the production method of the present invention, hydroxyalkylcellulose microparticles having a volume-average particle size of less than 15 μm can be obtained with ease.

Further, the hydroxyalkylcellulose microparticles can be used favorably in the production of solid preparations such as tablets using a direct compression method. By producing a solid preparation such as a tablet by a direct compression method using the hydroxyalkylcellulose microparticles of the present invention, the tensile strength of the solid preparation is increased, and the fluctuation in the disintegration properties caused by fluctuations in the compression pressure is reduced. Furthermore, by using the hydroxyalkylcellulose microparticles of the present invention, the bonding strength can be increased and the disintegration time of the solid preparation can be lengthened, meaning the preparation can be more easily imparted with sustained release properties.

MODES FOR CARRYING OUT THE INVENTION

Figure 1:
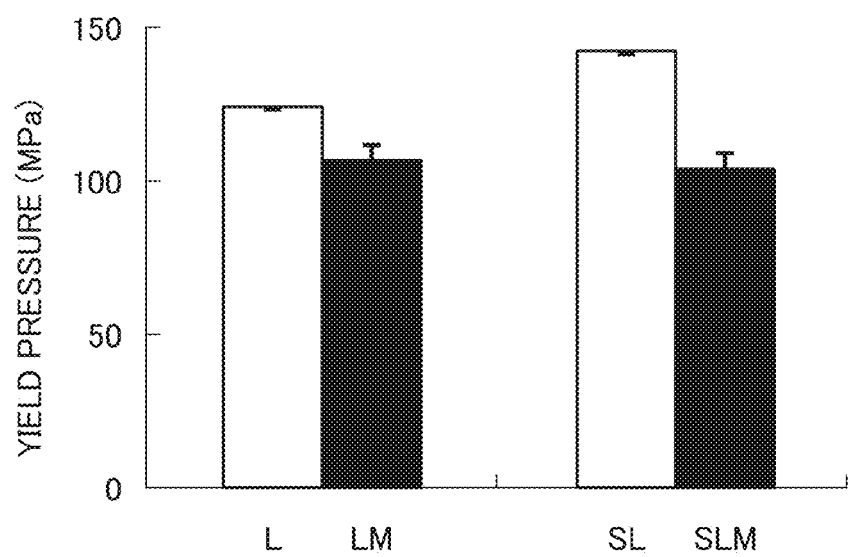
FIG. 1 is a diagram illustrating the yield pressure of hydroxyalkylcellulose microparticles.

The method of producing hydroxyalkylcellulose microparticles according to the present invention includes generating a pulse shock wave, and supplying a hydroxyalkylcellulose aqueous solution to the pulse shock wave generation region, thereby crushing and drying the hydroxyalkylcellulose aqueous solution. A crushing and drying apparatus containing a pulse combustor and a raw material supply port positioned close to the outlet of the exhaust pipe of the pulse combustor can be used favorably in this production method. A crushing and drying apparatus containing a pulse combustor and a raw material supply port positioned close to the outlet of the exhaust pipe of the pulse combustor, and also containing a gas regulation device which sets alternatively the particle Reynolds number of the exhaust gas from the pulse combustor that surrounds the particles of the supplied raw material to apply the continuously generated nonlinear waves to the raw material can be used particularly favorably.

The hydroxyalkylcellulose used in the present invention is obtained, for example, by reacting sodium hydroxide with a raw material cellulose to form an alkali cellulose, and then performing a substitution reaction between the alkali cellulose and an alkylene oxide. Following the substitution reaction, an acid such as acetic acid or hydrochloric acid is added to the reaction solution to neutralize the sodium hydroxide, and the product may then be purified. As a result of the substitution reaction, some or all of the —OH groups within the glucose ring units of the cellulose are substituted with —O—(R—O)$_m$—H groups. Here, R represents a divalent alkylene group. m is a natural number of 1 or greater.

Examples of alkylene oxides that can be used in the substitution reaction include ethylene oxide and propylene oxide. Of these, propylene oxide can be used particularly favorably in the present invention. When the substitution reaction is performed using propylene oxide, a hydroxypropylcellulose is obtained.

The hydroxyalkylcellulose supplied in the form of an aqueous solution has a hydroxyalkyl group content that is preferably within a range from 40 to 80% by weight, and more preferably within a range from 53 to 78% by weight. Further, the hydroxyalkylcellulose is preferably a hydroxypropylcellulose.

Moreover, the hydroxyalkylcellulose supplied as an aqueous solution has a viscosity at 20° C. for a 2% aqueous solution that is preferably within a range from 2.0 to 20.0 mPa·s, and more preferably within a range from 2.0 to 10.0 mPa·s.

The hydroxyalkylcellulose aqueous solution supplied to the pulse shock wave generation region has a concentration that is preferably within a range from 1 to 30% by weight, more preferably from 1 to 20% by weight, still more preferably from 1 to 10% by weight, and most preferably from 1 to 5% by weight.

The pulse shock waves (hereinafter also referred to as the "pulse jet" or the "nonlinear waves") are ultra-high sound pressure waves generated in association with the combustion in the pulse combustor. These ultra-high sound pressure waves typically exceed 150 dB. The pulse combustor has a combustion chamber and an exhaust pipe. Air and a fuel are supplied to the combustion chamber through respective supply pipes to form a mixed gas. Upon activation, a spark plug ignites the mixed gas in the combustion chamber. As a result of the combustion of the mixed gas, the combustion gas pressure increases, and that high-pressure gas is jetted from the exhaust pipe at high speed. Even following completion of the combustion, the action of inertia causes the jet to continue. The jet of combustion gases causes a negative pressure inside the combustion chamber, and as a result, fresh air and fuel are sucked into the combustion chamber and the high-temperature combustion gas inside the exhaust pipe flows back into the combustion chamber. Once the temperature of the pulse combustor has increased as a result of continuous operation, and the combustion gas has reached a sufficiently high temperature, the fresh mixed gas sucked into the combustion chamber self-ignites due to the back flow of the combustion gas, and the pulse combustor operates under continuous so-called "pulse combustion", in which explosions occur repeatedly, at a rate between one hundred and several tens of times through to several hundred times per second, even without using the spark plug. By providing a raw material supply port close to the outlet of the exhaust pipe of the pulse combustor, namely either inside or outside the tip of the exhaust pipe, and supplying the hydroxyalkylcellulose aqueous solution that represents the material to be dried through the raw material support port, the material to be dried is crushed as well as being dried via a solid-liquid separation due to the action of the pulse shock waves. The pulse shock waves combine a high sound pressure wave with a hot air stream generated by the combustion. As a result, the material to be dried can be dispersed into very fine particles and dried instantaneously as the air boundary layer at the particle surface is destroyed and any moisture in the vicinity of the particle surface is stripped away. These pulse shock waves are also described in Patent Document 5 and Patent Document 6.

In the present invention, the "particle Reynolds number" is a dimensionless quantity which, based on the difference in speed between a particle and a surrounding gas, represents the ratio between the viscous force imparted by the gas and the inertial force of the gas. In order to achieve a setting that enables the particle Reynolds number to be altered, the fuel supply volume, the primary air volume (the volume of air for combustion), the secondary air volume (the volume of air within the combustion gas or the volume of air blown around the combustion gas), the raw material supply volume or the raw material supply mode is operated. The raw material supply mode includes, for example, the injection pressure in those cases where the raw material is injected through a nozzle, the pressure and volume of the air or the like injected with the raw material, and the raw material particle size (primary particle size) at the time of injection which is determined by the above properties. There are no particular limitations on the gas regulation device which sets alternably the particle Reynolds number, and any device that enables the fuel supply volume, primary air volume, secondary air volume, raw material supply volume or raw material supply mode to be altered may be used.

The exhaust gas temperature within the region to which the hydroxyalkylcellulose aqueous solution is supplied is preferably within a range from 50 to 100° C., and more preferably within a range from 70 to 90° C. If the exhaust gas temperature is too high, then thermal degradation of the hydroxyalkylcellulose becomes more likely. If the temperature of the exhaust gas is too low, then the efficiency of the crushing and drying tends to deteriorate.

The hydroxyalkylcellulose microparticles of the present invention have a volume-average particle size that is preferably at least 0.1 μm but less than 15 μm, more preferably at least 0.1 μm but less than 10 μm, and still more preferably at least 1 μm but less than 9 μm. Although there are no particular limitations on the shape of the hydroxyalkylcellulose microparticles of the present invention, a spherical shape or a collapsed spherical shape, namely a shape with substantially no angular portions and having an overall rounded surface, is preferred. The volume-average particle size refers to the particle size $D_{50}$ at the point where the cumulative volume reaches 50% in a particle size distribution obtained by performing measurements using a laser scattering particle size distribution measurement device (for example, LDSA-2400 manufactured by Tonichi Computer Applications K.K.) under conditions including an air pressure of 3.0 $kgfcm^2$ and a focal length of 100 mm. Further, the particle shape can be confirmed by observation using a scanning electron microscope (for example, JSM-7330 manufactured by Jeol Ltd.).

In the hydroxyalkylcellulose microparticles of the present invention, the hydroxyalkyl group ($—(R—O)_m—H$) content is preferably within a range from 40 to 80% by weight, and more preferably from 53 to 78% by weight. Provided the hydroxyalkyl group content is within this range, a solid preparation having excellent tensile strength and disintegration properties can be more easily obtained. The particle shape tends to become closer to a spherical shape as the hydroxyalkyl group content decreases. The hydroxyalkyl group content can be determined using the method prescribed in USP24 (United States Pharmacopeia) or a method according to the method described in Patent Document 7. Furthermore, the hydroxyalkylcellulose microparticles are preferably hydroxypropylcellulose microparticles.

The hydroxyalkylcellulose microparticles of the present invention have a viscosity at 20° C. for a 2% aqueous solution of the hydroxyalkylcellulose microparticles that is within a range from 2.0 to 20.0 mPa·s, and more preferably within a range from 2.0 to 10.0 mPa·s. The viscosity is an indicator of the polymerization degree of the hydroxyalkylcellulose. Provided the viscosity falls within the type of range specified above, the workability associated with obtaining granules or tablets or the like is favorable. A higher viscosity tends to result in a slightly higher tensile strength for the obtained solid preparation. A lower viscosity tends to result in a shorter disintegration time for the obtained solid preparation.

The hydroxyalkylcellulose microparticles of the present invention can be used as a binder or molding base material for addition to solid preparations such as granules or tablets (including sugar-coated tablets, film-coated tablets, sublingual tablets and orally disintegratable tablets), as a binder for producing ceramics, as a film or coating agent, and also as a viscosity modifier, a dispersant or a tackifier or the like. Among these potential applications, the hydroxyalkylcellulose microparticles of the present invention are preferably used in solid preparations such as granules or tablets (including sugar-coated tablets, film-coated tablets, sublingual tablets and orally disintegratable tablets), and particularly preferably used in solid preparations prepared by dry direct compression methods.

A solid preparation of the present invention is prepared by formulating hydroxyalkylcellulose microparticles of the present invention having the aforementioned properties. In the present invention, a solid preparation refers to granules or tablets (including sugar-coated tablets, film-coated tablets, sublingual tablets and orally disintegratable tablets) or the like, and the solid preparation of the present invention is preferably a tablet (including sugar-coated tablets, film-coated tablets, sublingual tablets and orally disintegratable tablets). The solid preparation typically contains a principal agent as a medicinal component, and may also include additives such as excipients, binders, disintegrators, lubricants, sustained release agents, base materials, colorants, pH regulators, pH buffers, surfactants, stabilizers, acidifiers, flavorings and fragrances, fluidizers, algefacients, sweeteners, flavor enhancers and sweetness enhancers as required. In the solid preparation of the present invention, the hydroxyalkylcellulose microparticles are typically included as a material having the function of a binder or a base material.

Examples of the principal agent include medicinal drugs, agricultural chemicals and health food components and the like. Examples of the medicinal drugs include analgesics, antipyretic analgesics, headache treatment drugs, antitussives, expectorants, sedatives, antispasmodics, antihistamines, antiallergic agents, antiplasminic agents, bronchodilators, asthma treatment drugs, diabetes treatment drugs, liver disease treatment drugs, ulcer treatment drugs, gastritis treatment drugs, digestants, gastrointestinal motility activators, hypertension treatment drugs, angina treatment drugs, antihypertensive agents, hypotension treatment drugs, hyperlipidemia treatment agents, hormone drugs, antibiotics, antiviral drugs, sulfa drugs, anti-inflammatory agents, psychoneurosis drugs, intraocular pressure reducing agents, antiemetics, antidiarrheal drugs, gout treatment drugs, arrhythmia treatment drugs, vasoconstrictors, digestives, sleeping or hypnosis-inducing drugs, sympatholytics, anemia treatment drugs, antiepileptic drugs, anti-vertigo agents, disequilibrium treatment drugs, tuberculosis treatment drugs, vitamin deficiency treatment drugs, dementia treatment drugs, enuresis treatment drugs, anti-dizziness agents, oral bactericides, parasiticides, vitamins, amino acids and minerals. Among medicinal components, crude drug components generally exhibit poor tablet moldability, and therefore application of the solid preparation of the present invention is preferable.

Examples of the agricultural chemicals include antibacterial agents, antiviral agents, fungicides, miticides, insecticides, nematicides, rat poisons, herbicides, plant growth regulators, fertilizers and agents to reduce harmful effects of medicines.

There are no limitations on the health food components, provided they are substances to be formulated for the purpose of enhancing health, and specific examples thereof include green vegetable juice powder, aglycon, *agaricus*, ashwagandha, astaxanthin, acerola, amino acids (such as valine, leucine, isoleucine, lysine, methionine, phenylalanine, threonine, tryptophan, histidine, cystine, tyrosine, arginine, alanine, aspartic acid, powdered seaweed, glutamine, glutamic acid, glycine, proline and serine), alginic acid, *Ginkgo biloba* extract, sardine peptides, turmeric, uronic acid, echinacea, Siberian ginseng, oligosaccharides, oleic acid, nucleoproteins, dried skipjack peptides, catechin, potassium, calcium, carotenoids, *garcinia cambogia*, L-carnitine, chitosan, conjugated linoleic acid, Aloe arborescens, *Gymnema sylvestre* extract, citric acid, *Orthosiphon stamineus*, glycerides, glycenol, glucagon, glutamine, glucosamine, L-glutamine, *chlorella*, cranberry extract, *Uncaria tomentosa*, germanium, enzymes, Korean ginseng extract, coenzyme Q10, collagen, collagen peptides, Coleus forskolin, chondroitin, powdered psyllium husks, hawthorn extract, saponin, lipids, L-cystine, Japanese basil extract, citrimax, fatty acids, phytosterols, seed extracts, spirulina, squalene, *Salix alba*, ceramide, selenium, St. John's wort extract, soy isoflavone, soy saponin, soy peptides, soy lecithin, monosaccharides, proteins, chaste tree extract, iron, copper, docosahexaenoic acid, tocotrienol, nattokinase, *Bacillus natto* culture extract, sodium niacin, nicotinic acid, disaccharides, lactic acid bacteria, garlic, saw palmetto, rice sprouts, pearl barley extract, herb extracts, valerian extract, pantothenic acid, hyaluronic acid, biotin, chromium picolinate, vitamins A and A2, vitamins B 1, B2 and B6, vitamin B12, vitamin C, vitamin D, vitamin E, vitamin K, hydroxytyrosol, bifidobacteria, beer yeast, fructooligosaccharides, flavonoids, Butcher's broom extract, black cohosh, blueberry, prune extract, proanthocyanidin, proteins, propolis, bromelain, probiotics, phosphatidylcholine, phosphatidylserine, β-carotene, peptides, safflower extract, *Grifola frondosa* extract, maca extract, magnesium, *Silybum marianum*, manganese, mitochondria, minerals, mucopolysaccharides, melatonin, *Fomes yucatensis*, powdered melilot extract, molybdenum, vegetable powders, folic acid, lactose, lycopene, linoleic acid, lipoic acid, phosphorus, lutein, lecithin, rosmarinic acid, royal jelly, DHA and EPA.

Among the above additives, examples of excipients that may be added besides the hydroxyalkylcellulose include oligosaccharides (such as lactose), sugars, starches, processed starches, sugar alcohols (such as mannitol, sorbitol, xylitol and lactitol), inorganic acid salts, calcium sulfate, and aluminum and magnesium silicate complexes and oxides. Specific examples of the inorganic salt excipients include phosphoric salts such as calcium diphosphate dihydrate and hydrosulfates.

Examples of binders that may be added besides the hydroxyalkylcellulose include povidone, lactose, starches, processed starches, sugars, gum arabic, tragacanth gum, guar gum, pectin, wax-based binders, microcrystalline cellulose, methylcellulose, carboxymethylcellulose, copolyvidone, gelatin and sodium alginate.

Examples of disintegrators that may be added besides the hydroxyalkylcellulose include croscarmellose sodium, crospovidone, polyvinylpyrrolidone, sodium carboxymethyl starch, corn starch, and low-substituted degree hydroxypropylcellulose.

Examples of lubricants that may be added besides the hydroxyalkylcellulose include magnesium stearate, stearic acid, palmitic acid, calcium stearate, talc, carnauba wax, hydrogenated vegetable oils, mineral oils, polyethylene glycol, sodium stearyl fumarate and sucrose fatty acid esters (of stearic acid, palmitic acid, myristic acid, oleic acid, lauric acid, behenic acid and erucic acid and the like).

Examples of sustained release agents that may be added besides the hydroxyalkylcellulose include sodium alginate, carboxy vinyl polymers, and acrylic acid-based polymers such as aminoalkyl methacrylate copolymer RS (Eudragit RS (product name), manufactured by Rohm Pharma GmbH) and ethyl acrylate-methyl methacrylate copolymer suspension (Eudragit NE (product name, manufactured by Rohm Pharma GmbH).

Examples of base materials that may be added besides the hydroxyalkylcellulose include sugar coating base materials, water-soluble film coating base materials, enteric film coating base materials and sustained release film coating base materials.

Examples of the sugar coating base material include white soft sugar, talc, precipitated calcium carbonate, calcium phosphate, calcium sulfate, gelatin, gum arabic, polyvinylpyrrolidone and pullulan.

Examples of the water-soluble film coating base materials include: synthetic polymer compounds such as polyvinyl alcohol, polyvinyl alcohol-polyethylene glycol graft copolymers, polyvinyl alcohol-acrylic acid-methyl methacrylate copolymers, polyvinyl acetal diethylaminoacetate, aminoalkyl methacrylate copolymers, polyvinylpyrrolidone and macrogol; and polysaccharides such as pullulan.

Examples of the enteric film coating base materials include: acrylic acid derivatives such as methacrylic acid copolymer L, methacrylic acid copolymer LD and methacrylic acid copolymer S; and natural materials such as shellac.

Examples of the sustained release film coating base materials include acrylic acid derivatives such as aminoalkyl methacrylate copolymer RS and ethyl acrylate-methyl methacrylate copolymer emulsion.

Examples of colorants that may be added besides the hydroxyalkylcellulose include food dyes such as food yellow No. 5, food red No. 2 and food blue No. 2, food lake dyes, and iron sesquioxide.

Examples of pH regulators that may be added besides the hydroxyalkylcellulose include any compounds for pharmaceutical use, and specific examples thereof include inorganic acids such as hydrochloric acid, sulfuric acid, hydrobromic acid and phosphoric acid, organic acids such as acetic acid, succinic acid, fumaric acid, malic acid, oxalic acid, lactic acid, glutaric acid, salicylic acid and tartaric acid, and salts thereof.

Examples of pH buffers that may be added besides the hydroxyalkylcellulose include amine-based buffers and carbonate-based buffers.

Examples of surfactants that may be added besides the hydroxyalkylcellulose include sodium lauryl sulfate, polysorbate 80, hydrogenated oil, and polyoxyethylene (160) polyoxypropylene (30) glycol.

Examples of stabilizers that may be added besides the hydroxyalkylcellulose include tocopherol, tetrasodium edetate, nicotinamide and cyclodextrins.

Examples of acidifiers that may be added besides the hydroxyalkylcellulose include citric acid, tartaric acid, malic acid and ascorbic acid.

Examples of flavorings and fragrances that may be added besides the hydroxyalkylcellulose include: various fragrances of fruit, such as strawberry, or yoghurt; lemon oil, orange oil, and menthol.

Examples of fluidizer that may be added besides the hydroxyalkylcellulose include light anhydrous silicic acid, hydrated silicone dioxide and talc.

Examples of algefacients that may be added besides the hydroxyalkylcellulose include terpene-based compounds (such as monoterpene alcohol) such as menthol, camphor, and borneol.

Examples of sweeteners that may be added besides the hydroxyalkylcellulose include: artificial and natural sweeteners, such as aspartame, acesulfame potassium, saccharin, sodium saccharin, sucralose, sugar sweeteners (such as xylose, ribose, glucose, mannose, galactose, fructose, dextrose, sucrose, maltose and partially hydrogenated starches (such as maltitol syrup and corn syrup solid)), sugar alcohols (such as sorbitol, xylitol, mannitol and glycerin), and combinations thereof.

Examples of flavor enhancers that may be added besides the hydroxyalkylcellulose include glutamic acid, inosinic acid, and salts thereof Examples of sweetness enhancers that may be added besides the hydroxyalkylcellulose include sodium chloride, potassium chloride, organic acid salts and phosphoric salts.

There are no particular limitations on the amount of the hydroxyalkylcellulose microparticles in the solid preparation of the present invention, but the amount is preferably within a range from 0.5 to 15% by weight, and more preferably from 1 to 10% by weight, of the solid preparation.

There are no particular limitations on the method for producing the solid preparation. Examples thereof include: a method in which an excipient, a disintegrator, and the like are added to and mixed with the principal agent, a binder (the hydroxyalkylcellulose microparticles) is added to and kneaded with the mixture, the kneaded mixture is granulated using a granulator, the resulting granules are dried and graded, a lubricant such as magnesium stearate is mixed with the graded granules, and then the resulting mixture is subjected to tablet compression (namely, a wet granule tableting method or dry granule tableting method); and a method in which the principal agent is mixed with an excipient and a base material (the hydroxyalkylcellulose microparticles), a lubricant is mixed therewith, and the resulting mixture is then subjected to tablet compression (namely, a dry direct tableting method). Among the methods, the dry direct tableting method or a dry granule tableting method is preferably employed in the present invention.

EXAMPLES

The present invention is described below in further detail based on a series of examples. However, the present invention is in no way limited by these examples.

In the following example, physical properties were evaluated using the methods described below.

10% by weight of hydroxypropylcellulose microparticles or a bulk powder, 0.5% by weight of a silica (SYLYSIA 350, manufactured by Fuji Silysia Chemical Ltd.), 1% by weight of magnesium stearate and 88.5% by weight of erythritol were mixed together thoroughly to obtain a preparation A.

A mortar having a diameter of 8 mm that had been externally lubricated using an acetone suspension of magnesium stearate (10 mg/ml) was packed with 200 mg of the aforementioned preparation A, and a universal tension and compression testing machine (AUTOGRAPH, manufactured by Shimadzu Corporation) was used to compress the preparation under conditions including a compression pressure of 100 MPa and a compression speed of 10 mm/minute. The cycle energy (CE) and expansion energy (EE) were determined, and EE/CE (%) was calculated using the formula below.

$$EE/CE(\%)=[(\text{Expansion Energy})/(\text{Cycle Energy})]\times 100$$

Figure 11:
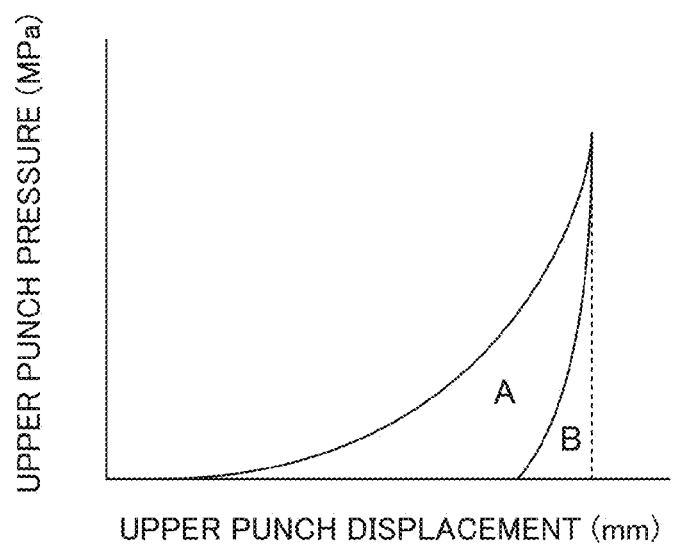
FIG. 11 is a diagram explaining Expansion Energy (EE) and Cycle Energy (CE).

The region B in FIG. 11 corresponds with EE, and the region composed of a combination of A and B corresponds with CE.

A mortar having a diameter of 8 mm was packed with 200 mg of the preparation A, a tableting process analyzer (Tab-All, manufactured by Okada Seiko Co., Ltd.) was used to compress the preparation under conditions including a compression pressure of 200 MPa and a compression speed of 10 spm, and the yield pressure was determined on the basis of the Heckel equation. This test yielded a tablet A.

$$\ln(1/(1-D))=K\times P+A \quad \text{[Heckel Equation]}$$

D represents the apparent relative density, P represents the compression pressure (MPa), K represents the slope of the straight line portion obtained by plotting the compression pressure P in an x axis and the value of ln(1(1−D)) in a y axis, and A represents the value obtained when the straight line portion is extrapolated to the point where the compression pressure P=0 MPa (namely, the y-axis intercept of the extrapolated straight line). The yield pressure is calculated as the value of 1/K.

For the tablet A, a load cell-type tablet hardness meter (PORTABLE CHECKER PC-30, manufactured by Okada Seiko Co., Ltd.) was used to measured the hardness under conditions including a fracture speed of 30 mm/minute (in the diameter direction), and the tensile strength of the tablet was calculated using the following equation.

$$TS = 2P/(\pi DT)$$

TS represents the tensile strength (MPa) of the tablet, P represents the hardness (N) of the tablet, $\pi$ is the ratio of circumference to diameter, D represents the diameter (mm) of the tablet, and T represents the thickness (mm) of the tablet.

Further, in accordance with the disintegration test method prescribed in the fifteenth edition of The Japanese Pharmacopoeia, 200 mg of the tablet was placed in purified water at 37° C., and the disintegration time was measured.

Example 1

Preparation of Hydroxyalkylcellulose Microparticles

Figure 12:
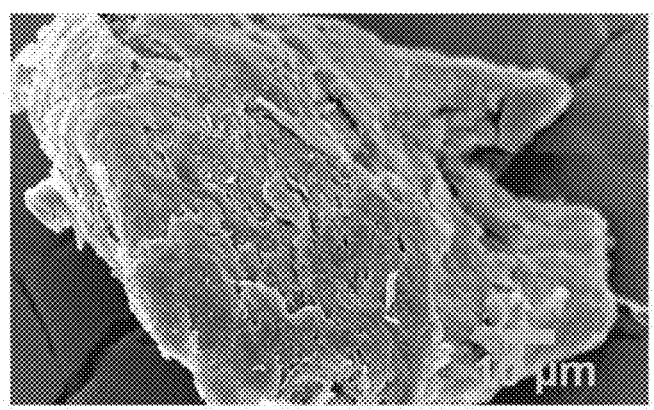
FIG. 12 is a diagram illustrating a scanning electron microscope photograph of a bulk powder of a hydroxypropylcellulose HPC L.

A hydroxypropylcellulose bulk powder conforming to the Japanese Pharmacopoeia ("HPC L" manufactured by Nippon Soda Co., Ltd., viscosity at 20° C. of a 2% aqueous solution: 6.0 to 10.0 mPa·s) was dissolved in water to prepare aqueous solutions having concentrations of 1%, 2%, 5% and 10% respectively. The bulk powder of the hydroxypropylcellulose HPC L had a volume-average particle size of 103.6 μm and was amorphous (see FIG. 12).

Each of the above hydroxypropylcellulose aqueous solutions was supplied to a crushing and drying apparatus having a pulse combustor (HYPULCON, manufactured by Ohkawara Kakohki Co., Ltd.), and the pulse jet was applied to the aqueous solution to achieve crushing and drying. The exhaust gas temperature in the region to which the aqueous solution was supplied was set at 80° C.

Figure 13:
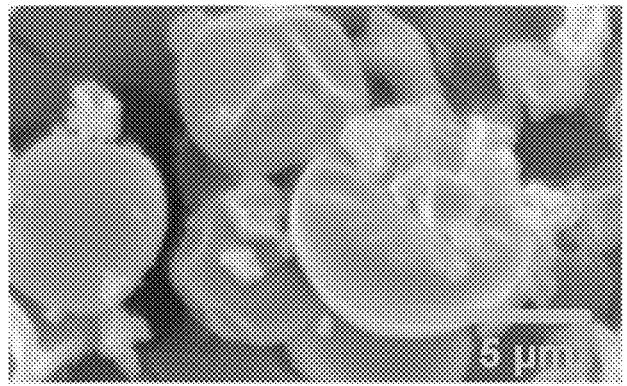
FIG. 13 is a diagram illustrating a scanning electron microscope photograph of hydroxypropylcellulose microparticles obtained from a 2% aqueous solution in Example 1.

This crushing and drying yielded hydroxypropylcellulose microparticles. These microparticles were all slightly flattened spherical shapes (see FIG. 13). The particle sizes $D_{16}$, $D_{50}$ and $D_{84}$ of each sample of microparticles were as shown in Table 1. The viscosity at 20° C. of a 2% aqueous solution of the obtained hydroxypropylcellulose microparticles was the same as that of the bulk powder in each case, confirming that no thermal degradation of the hydroxypropylcellulose itself had occurred during the drying process.

TABLE 1

| | Particle size [μm] | | |
|---|---|---|---|
| | $D_{16}$ | $D_{50}$ | $D_{84}$ |
| Example 1 | | | |
| Bulk powder HPC L | 41.0 ± 2.4 | 103.6 ± 6.7 | 192.9 ± 14.7 |
| 1% aqueous solution | 3.6 ± 0.5 | 7.2 ± 0.6 | 12.2 ± 1.3 |
| 2% aqueous solution | 3.8 ± 0.2 | 6.5 ± 0.5 | 9.7 ± 0.8 |
| 5% aqueous solution | 3.9 ± 0.4 | 6.0 ± 0.3 | 8.7 ± 0.3 |
| 10% aqueous solution | 2.9 ± 0.1 | 5.5 ± 0.2 | 8.6 ± 0.6 |

Example 2

With the exception of replacing the 2% aqueous solution of the hydroxypropylcellulose from Example 1 with a 2% aqueous solution of a hydroxypropylcellulose ("HPC SL" manufactured by Nippon Soda Co., Ltd., viscosity at 20° C. of the 2% aqueous solution: 3.0 to 5.9 mPa·s), hydroxypropylcellulose microparticles were obtained using the same procedure as that described for Example 1. The particle sizes $D_{16}$, $D_{50}$ and $D_{84}$ of the microparticles were as shown in Table 2. The microparticles were slightly flattened spherical shapes. The viscosity at 20° C. of a 2% aqueous solution of the obtained hydroxypropylcellulose microparticles was the same as that of the bulk powder. The bulk powder of the hydroxypropylcellulose HPC SL had a volume-average particle size of 83.3 μm and had an angular irregular-shape.

Example 3

Figure 14:
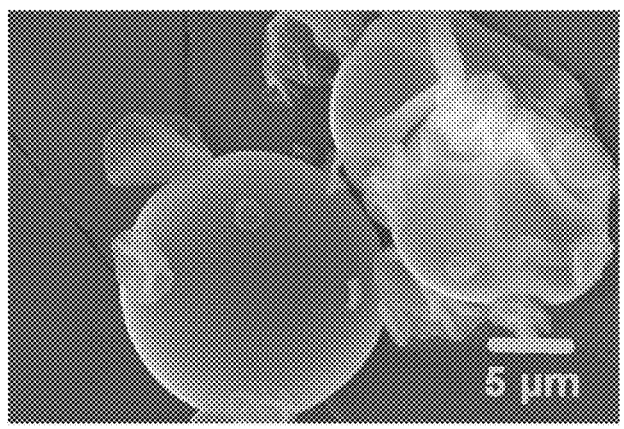
FIG. 14 is a diagram illustrating a scanning electron microscope photograph of hydroxypropylcellulose microparticles obtained from a 10% aqueous solution in Example 3.
Figure 15:
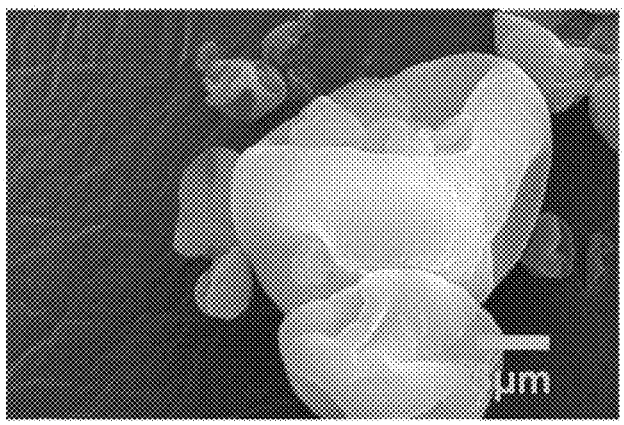
FIG. 15 is a diagram illustrating a scanning electron microscope photograph of hydroxypropylcellulose microparticles obtained from a 20% aqueous solution in Example 3.

With the exception of using 10% or 20% aqueous solutions of the hydroxypropylcellulose ("HPC L" manufactured by Nippon Soda Co., Ltd., viscosity at 20° C. of a 2% aqueous solution: 6.0 to 10.0 mPa·s), hydroxypropylcellulose microparticles were obtained using the same procedure as that described for Example 1. The particle sizes $D_{16}$, $D_{50}$ and $D_{84}$ of the microparticles were as shown in Table 2. The microparticles had slightly flattened spherical shapes (see FIG. 14 and FIG. 15). The viscosity at 20° C. of a 2% aqueous solution of the obtained hydroxypropylcellulose microparticles was the same as that of the bulk powder.

TABLE 2

| | Particle size [μm] | | |
|---|---|---|---|
| | $D_{16}$ | $D_{50}$ | $D_{84}$ |
| Example 2 | | | |
| Bulk powder HPC SL | 33.4 ± 1.7 | 83.3 ± 3.3 | 160.6 ± 5.4 |
| 2% aqueous solution | 3.9 ± 0.2 | 7.5 ± 0.7 | 12.6 ± 2.9 |
| Example 3 | | | |
| 10% aqueous solution | 6.1 ± 0.1 | 11.6 ± 0.7 | 23.6 ± 1.5 |
| 20% aqueous solution | 7.1 ± 0.2 | 13.9 ± 1.3 | 26.6 ± 4.9 |

Example 4

Figure 16:
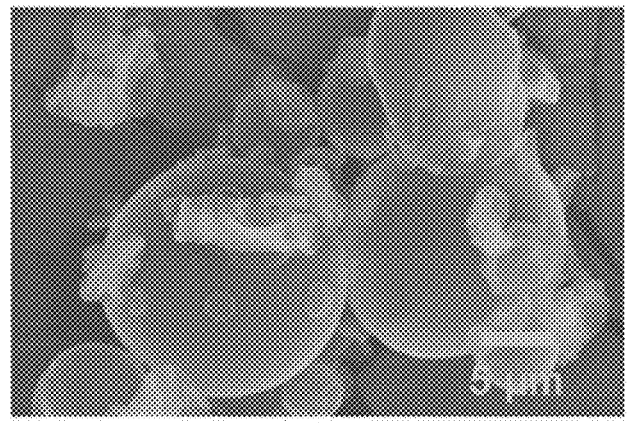
FIG. 16 is a diagram illustrating a scanning electron microscope photograph of hydroxypropylcellulose microparticles obtained from a 20% aqueous solution in Example 4.

With the exception of replacing the 20% aqueous solution of the hydroxypropylcellulose from Example 3 with a 20% aqueous solution of a hydroxypropylcellulose ("HPC SSL" manufactured by Nippon Soda Co., Ltd., viscosity at 20° C. of a 2% aqueous solution: 2.0 to 2.9 mPa·s), hydroxypropylcellulose microparticles were obtained using the same procedure as that described for Example 3. The particle sizes $D_{16}$, $D_{50}$ and $D_{84}$ of the microparticles were as shown in Table 3. The microparticles had slightly flattened spherical shapes (see FIG. 16). The viscosity at 20° C. of a 2% aqueous solution of the obtained hydroxypropylcellulose microparticles was the same as that of the bulk powder. The bulk powder of the hydroxypropylcellulose HPC SSL had angular irregular-shapes.

Comparative Example 1

Figure 17:
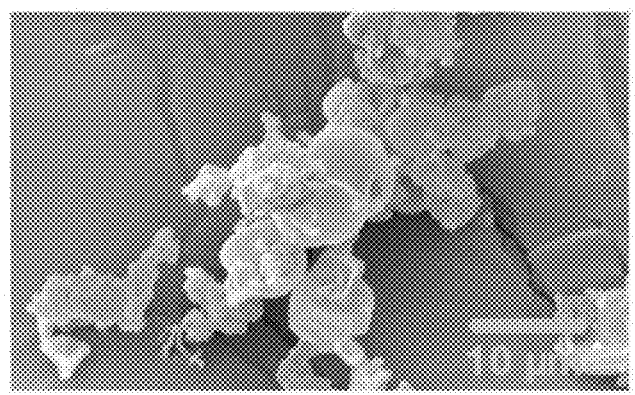
FIG. 17 is a diagram illustrating a scanning electron microscope photograph of hydroxypropylcellulose microparticles obtained in Comparative example 1.

A 1% aqueous solution of hydroxypropylcellulose ("HPC L" manufactured by Nippon Soda Co., Ltd., viscosity at 20° C. of a 2% aqueous solution: 6.0 to 10.0 mPa·s) was dried at 150° C. using a spray drying method. This drying yielded a hydroxypropylcellulose SD1. The shape of the SD1 was shown in FIG. 17. The particle sizes $D_{16}$, $D_{50}$ and $D_{84}$ of SD1 were as shown in Table 3.

Comparative Example 2

Figure 18:
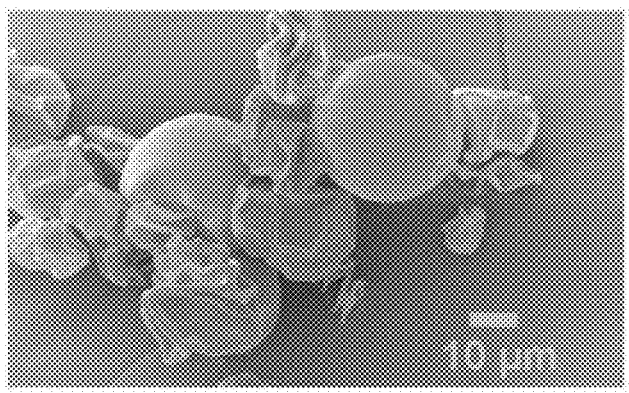
FIG. 18 is a diagram illustrating a scanning electron microscope photograph of hydroxypropylcellulose microparticles obtained in Comparative example 2.

With the exceptions of altering the concentration of the aqueous solution to 2% and altering the drying temperature used in the spray drying method to 180° C., a hydroxypropylcellulose SD2 was obtained using the same procedure as that described for Comparative example 1. The shape of the SD2 was shown in FIG. 18. The particle sizes $D_{16}$, $D_{50}$ and $D_{84}$ of SD2 were as shown in Table 3.

TABLE 3

|  | Particle size [μm] | | |
| --- | --- | --- | --- |
|  | $D_{16}$ | $D_{50}$ | $D_{84}$ |
| Example 4 |  |  |  |
| 20% aqueous solution Comparative Example 1 | 5.9 ± 0.6 | 13.3 ± 1.9 | 26.2 ± 6.3 |
| SD1 Comparative Example 2 | 4.8 ± 0.1 | 10.5 ± 0.6 | 20.8 ± 1.3 |
| SD2 | 14.1 ± 0.5 | 27.1 ± 1.6 | 47.8 ± 4.3 |

The hydroxypropylcellulose bulk powder HPC L (hereinafter abbreviated as "L"), the hydroxypropylcellulose microparticles having a volume-average particle size of 6.5 μm obtained in Example 1 (hereinafter abbreviated as "LM"), the hydroxypropylcellulose bulk powder HPC SL (hereinafter abbreviated as "SL"), the hydroxypropylcellulose microparticles having a volume-average particle size of 7.5 μm obtained in Example 2 (hereinafter abbreviated as "SLM"), the hydroxypropylcellulose microparticles having a volume-average particle size of 11.6 μm obtained in Example 3 (hereinafter abbreviated as "L10"), the hydroxypropylcellulose microparticles having a volume-average particle size of 13.9 μm obtained in Example 3 (hereinafter abbreviated as "L20"), the hydroxypropylcellulose bulk powder HPC SSL (hereinafter abbreviated as "SSL"), the hydroxypropylcellulose microparticles having a volume-average particle size of 13.3 μm obtained in Example 4 (hereinafter abbreviated as "SSL20"), the hydroxypropylcellulose having a volume-average particle size of 10.5 μm obtained in Comparative example 1 (hereinafter abbreviated as "SD1"), and the hydroxypropylcellulose having a volume-average particle size of 27.1 μm obtained in Comparative example 2 (hereinafter abbreviated as "SD2") were evaluated in terms of physical properties. The results are shown in FIG. 1 to FIG. 9.

Figure 2:
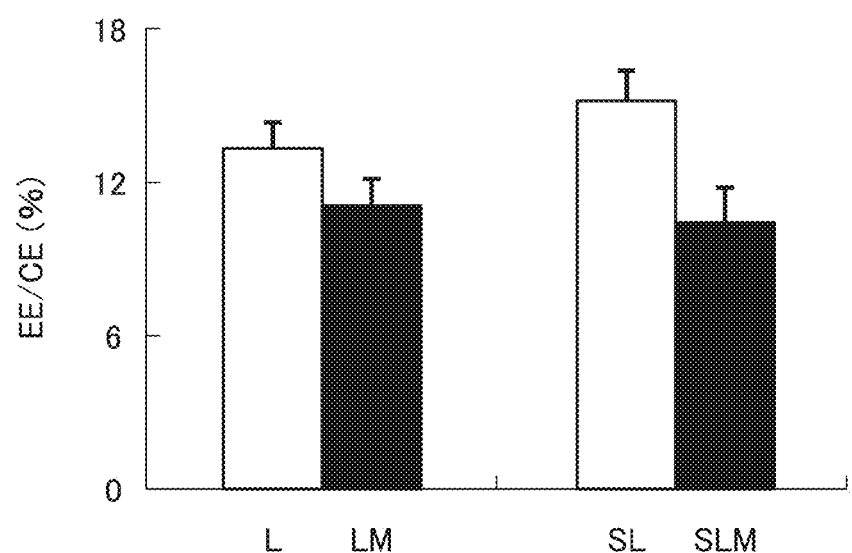
FIG. 2 is a diagram illustrating the EE/CE value of hydroxyalkylcellulose microparticles.

Based on FIG. 1 and FIG. 2, it is evident that by using the hydroxypropylcellulose microparticles (LM or SLM) of the present invention, the yield pressure and the EE/CE value decreased, resulting in more favorable workability during tablet compression.

Figure 3:
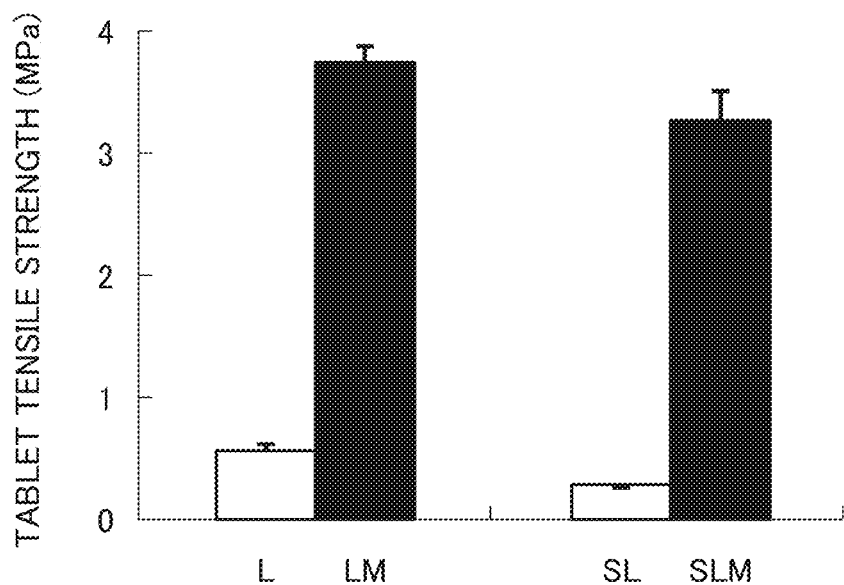
FIG. 3 is a diagram illustrating the tensile strength of tablets obtained using hydroxyalkylcellulose.
Figure 4:
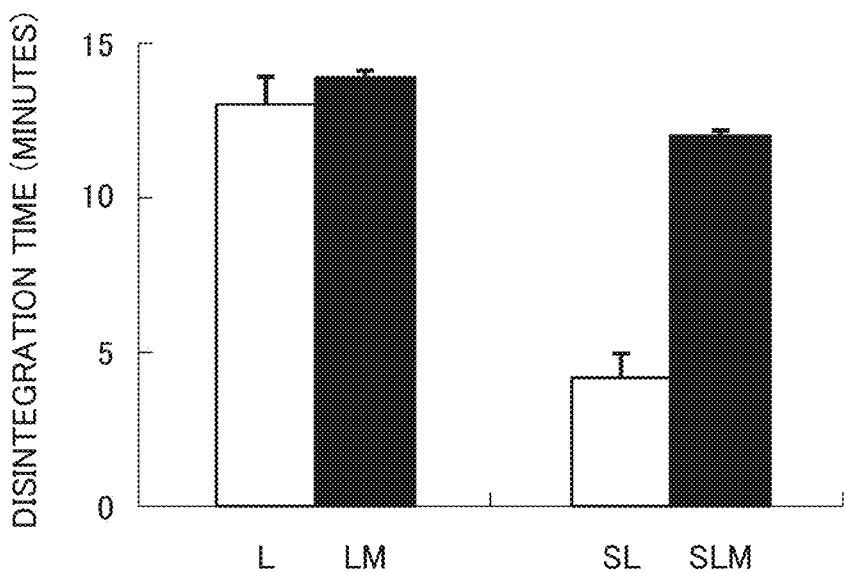
FIG. 4 is a diagram illustrating the disintegration time of tablets obtained using hydroxyalkylcellulose.

Further, based on FIG. 3 and FIG. 4, it is evident that tablets formed using the hydroxypropylcellulose microparticles (LM or SLM) of the present invention had a higher tensile strength and a longer disintegration time. In the comparison of SL and SLM, which both used the hydroxypropylcellulose having a viscosity at 20° C. for a 2% aqueous solution of 3.0 to 5.9 mPa·s, a marked difference was observed in the disintegration time.

Figure 5:
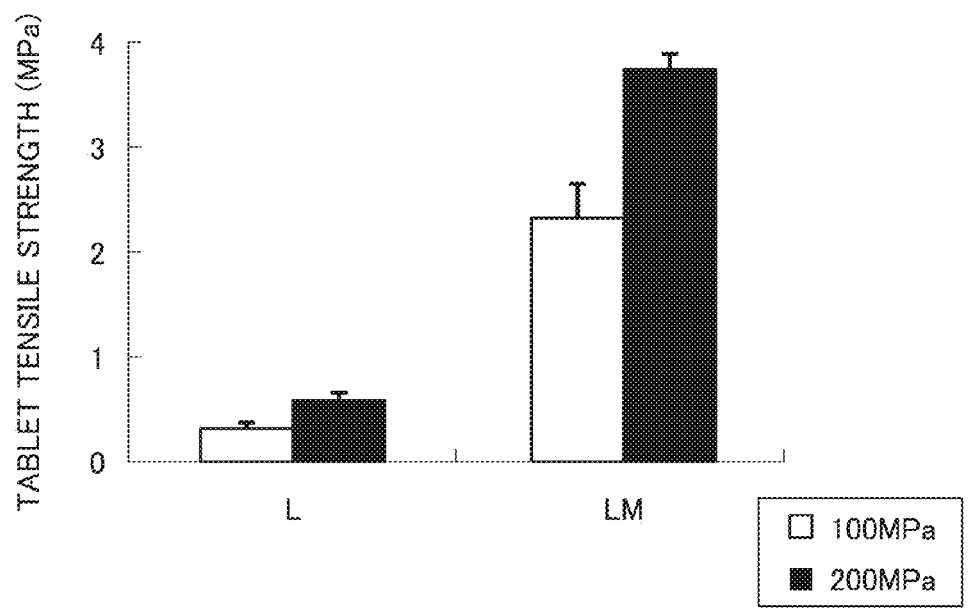
FIG. 5 is a diagram illustrating the effect that a difference in the compression pressure has on the tensile strength of tablets.
Figure 6:
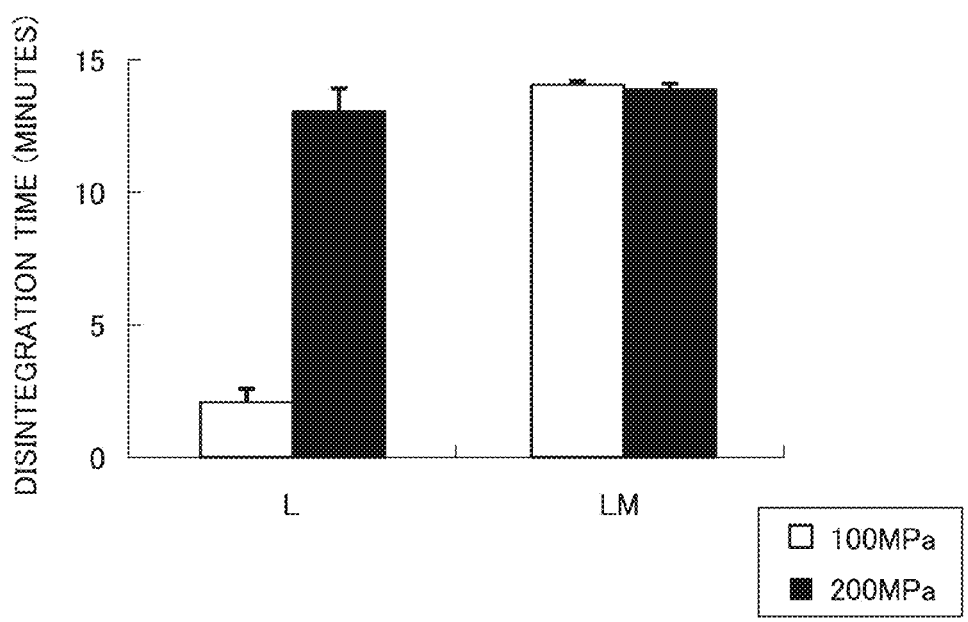
FIG. 6 is a diagram illustrating the effect that a difference in the compression pressure has on the disintegration time of tablets.

The tensile strength and disintegration time were compared for tablets obtained by performing tablet compression at a compression pressure of 100 MPa and tablets obtained by performing tablet compression at a compression pressure of 200 MPa (see FIG. 5 and FIG. 6). It is clear from the results that use of the hydroxypropylcellulose microparticles (LM) of the present invention yielded a significant increase in the tensile strength. Further, by using the hydroxypropylcellulose microparticles (LM) of the present invention, the disintegration time became unaffected by the compression pressure. Based on the results, it is evident that even if the tablet compression conditions fluctuate, fluctuation in the sustained release properties of the tablet is unlikely.

Figure 7:
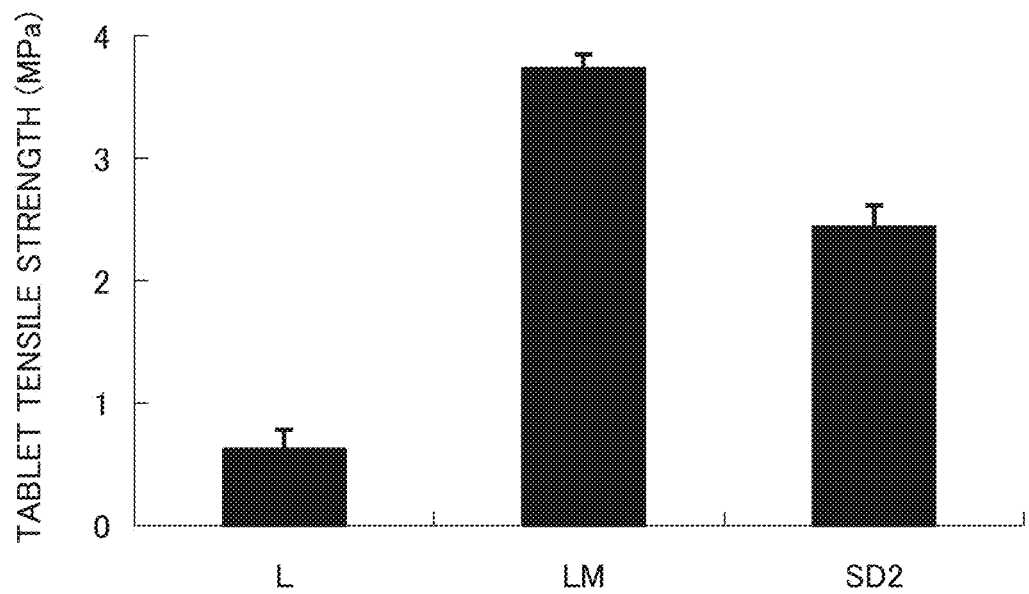
FIG. 7 is a diagram illustrating the effect that a difference in the method of producing the hydroxyalkylcellulose microparticles has on the tensile strength of tablets.

Moreover, as shown in FIG. 7, although the tablets formed using the hydroxypropylcellulose (SD2) obtained by a spray drying method that represents a typical conventional drying method exhibited an increase in tensile strength compared with the tablets formed directly using the bulk powder, the tensile strength was still considerably lower than that of the tablets formed using the hydroxypropylcellulose microparticles (LM) of the present invention.

Figure 8:
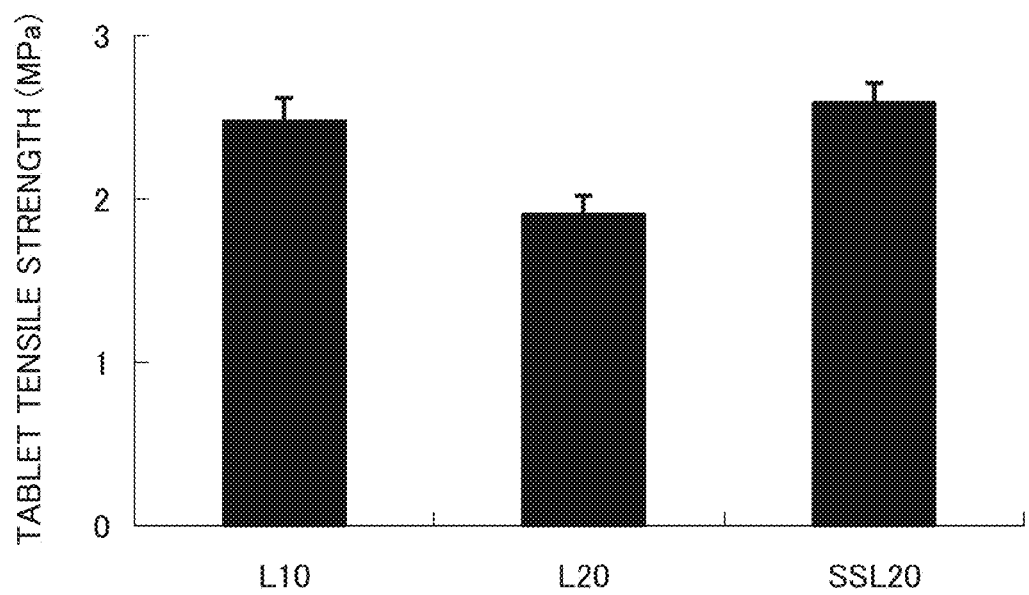
FIG. 8 is a diagram illustrating the effect that differences in the viscosity of the hydroxyalkylcellulose and the concentration of the aqueous solution supplied to the drying process have on the tensile strength of tablets.
Figure 9:
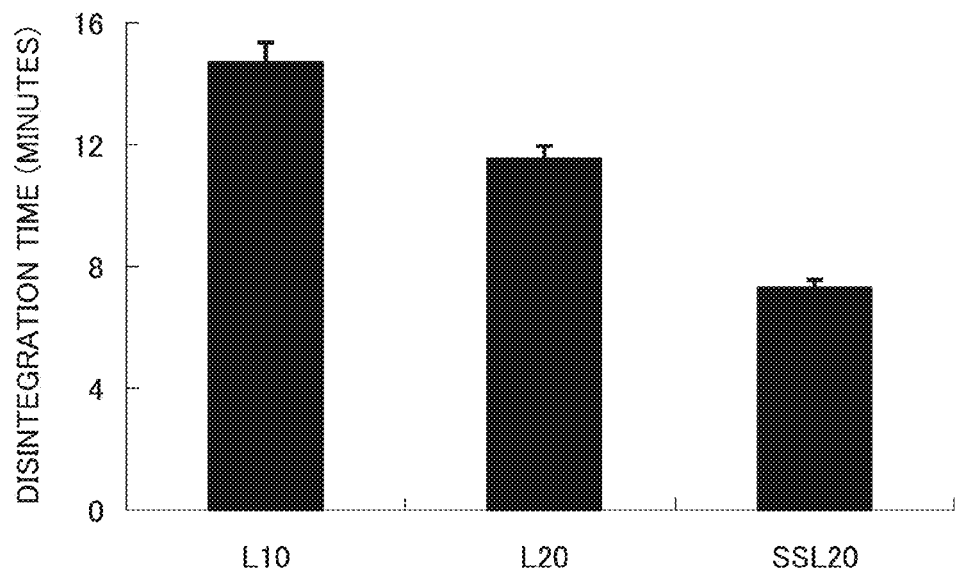
FIG. 9 is a diagram illustrating the effect that differences in the viscosity of the hydroxyalkylcellulose and the concentration of the aqueous solution supplied to the drying process have on the disintegration time of tablets.

As illustrated in FIG. 8 and FIG. 9, it is evident that the strength and disintegration time of the tablets were alterable by adjusting the viscosity at 20° C. of a 2% aqueous solution of the microparticles and/or the concentration of the aqueous solution supplied to the crushing and drying process.

Example 5

3% by weight of hydroxypropylcellulose microparticles (LM), 0.5% by weight of a silica (SYLYSIA 350, manufactured by Fuji Silysia Chemical Ltd.), 1% by weight of magnesium stearate, 10% by weight, 15% by weight or 20% by weight of crospovidone (disintegrator), and 85.5% by weight, 80.5% by weight or 75.5% by weight of erythritol were mixed together thoroughly to obtain preparations B-1, B-2 and B-3 respectively.

Figure 10:
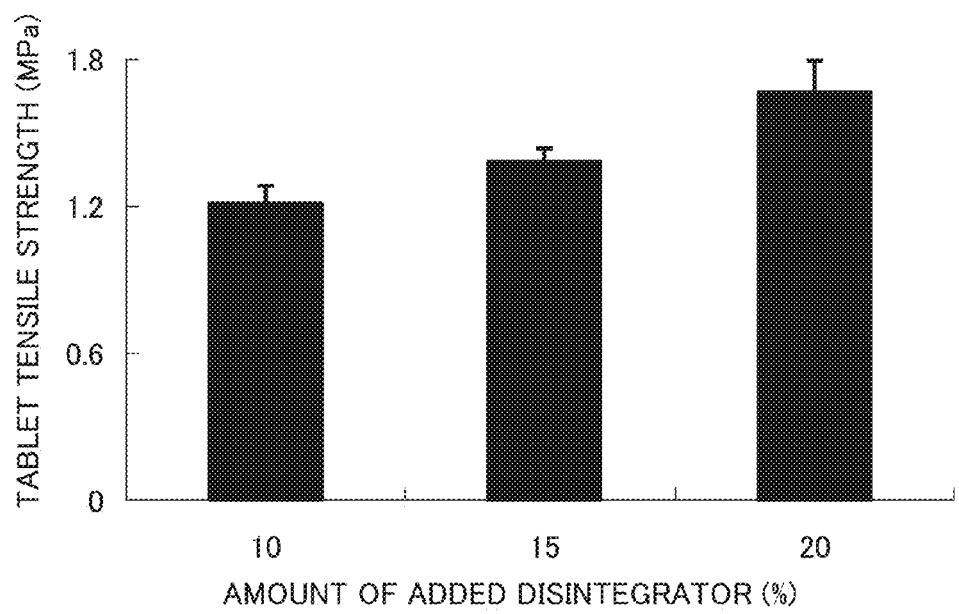
FIG. 10 is a diagram illustrating the effect that adding a disintegrator has on the tensile strength of tablets.

With the exception of using the preparations B-1, B-2 and B-3, tablets B-1, B-2 and B-3 were obtained using the same procedure as that described above for the method of producing the tablet A. For each of the tablets, the tablet tensile strength was determined using the same procedure as that described above. The results are shown in FIG. 10. It is evident that addition of the disintegrator further increased the tensile strength. Further, the preparations B-1, B-2 and B-3 each had a disintegration time of 30 seconds or less in the disintegration test described above.

Example 6 and Comparative Example 3

Figure 19:
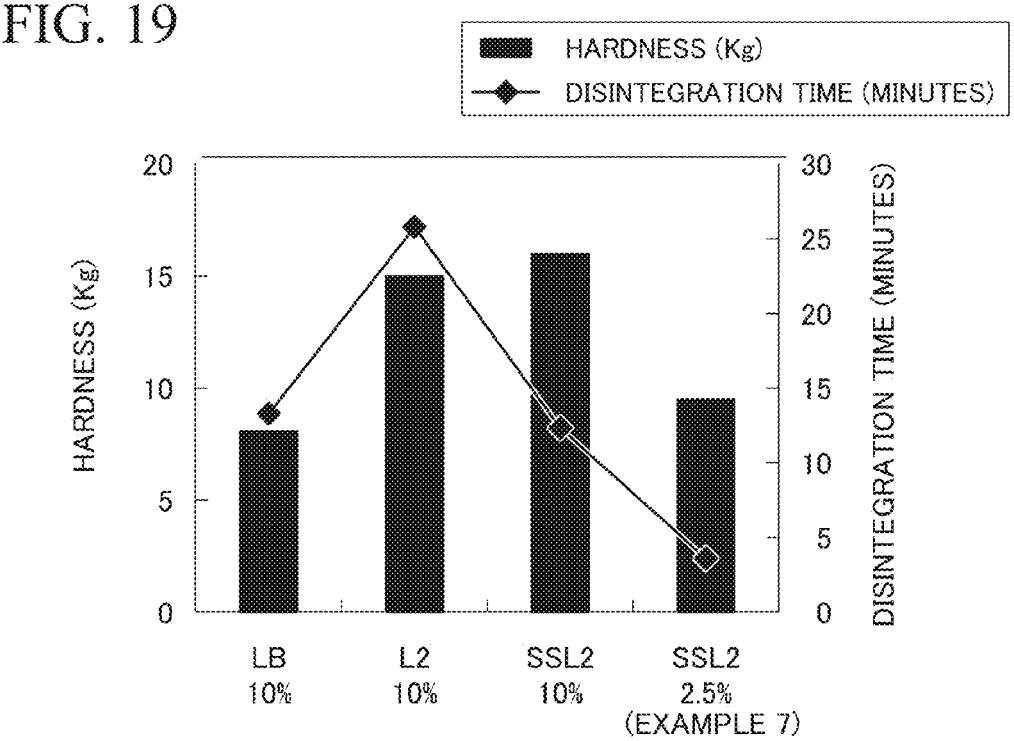
FIG. 19 is a diagram illustrating the hardness and disintegration time of tablets containing lactose and corn starch obtained in Example 6, Example 7, and Comparative example 3.

10% by weight of a hydroxypropylcellulose, 63% by weight of lactose (Dailactose S, manufactured by Freund Corporation), 27% by weight of a corn starch (Corn Starch W, manufactured by Nihon Shokuhin Kako Co., Ltd.) and 0.5% by weight of magnesium stearate (in outer percentage) were mixed together thoroughly to obtain a preparation C. With the exception of using the preparation C, a tablet C was obtained using the same procedure as that described above for the method of producing the tablet A. For the tablet C, the tablet hardness and disintegration time were determined using the same procedures as described above. These results are shown in FIG. 19.

Figure 20:
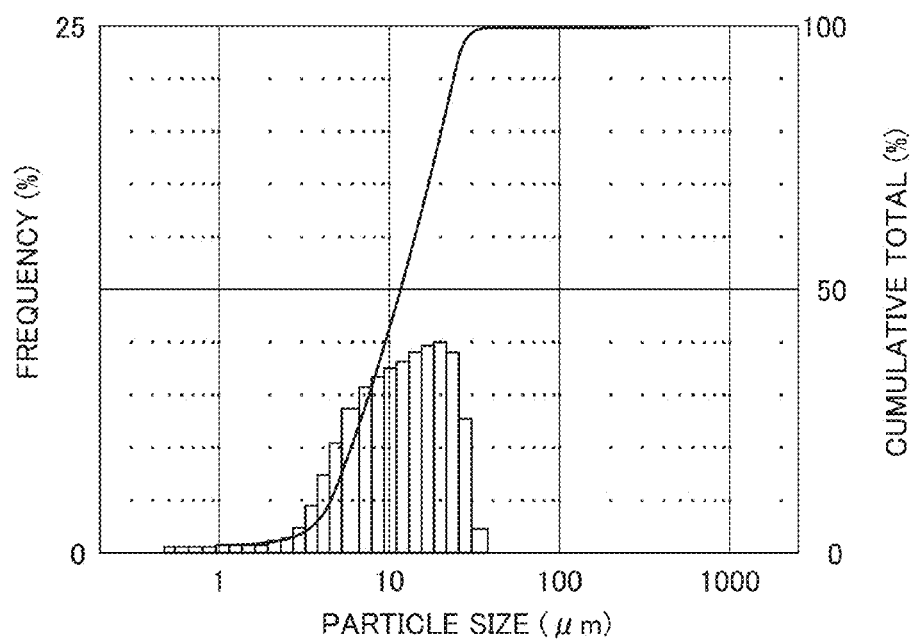
FIG. 20 is a diagram illustrating the particle size distribution of hydroxypropylcellulose microparticles SSL2.

For the hydroxypropylcellulose, hydroxypropylcellulose microparticles L2 having a volume-average particle size of 12 μm obtained using the same procedure as that described for Example 3, hydroxypropylcellulose microparticles SSL2 having a volume-average particle size of 12 μm obtained using the same procedure as that described for Example 4, and a hydroxypropylcellulose obtained by passing the hydroxypropylcellulose bulk powder HPC L through a 100-mesh (hereinafter abbreviated as LB, volume-average particle size: 44 nm) were used, respectively. The particle size distribution of the hydroxypropylcellulose microparticles SSL2 is shown in FIG. 20.

Example 7

2.5% by weight of a hydroxypropylcellulose, 73.1% by weight of lactose (Dailactose S, manufactured by Freund Corporation), 24.4% by weight of a corn starch (Corn Starch W, manufactured by Nihon Shokuhin Kako Co., Ltd.) and 0.5% by weight of magnesium stearate (in outer percentage) were mixed together thoroughly to obtain a preparation D. With the exception of using the preparation D, a tablet D was obtained using the same procedure as that described above for the method of producing the tablet A. For the tablet D, the tablet hardness and disintegration time were determined using the same procedures as described above. These results are shown in FIG. 19.

For the hydroxypropylcellulose, hydroxypropylcellulose microparticles SSL2 having a volume-average particle size of 12 μm obtained using the same procedure as that described for Example 4 were used. It is evident that by adding a small amount of the hydroxypropylcellulose microparticles SSL2, tablets having a high degree of hardness and a short disintegration time can be obtained.

Example 8

Figure 21:
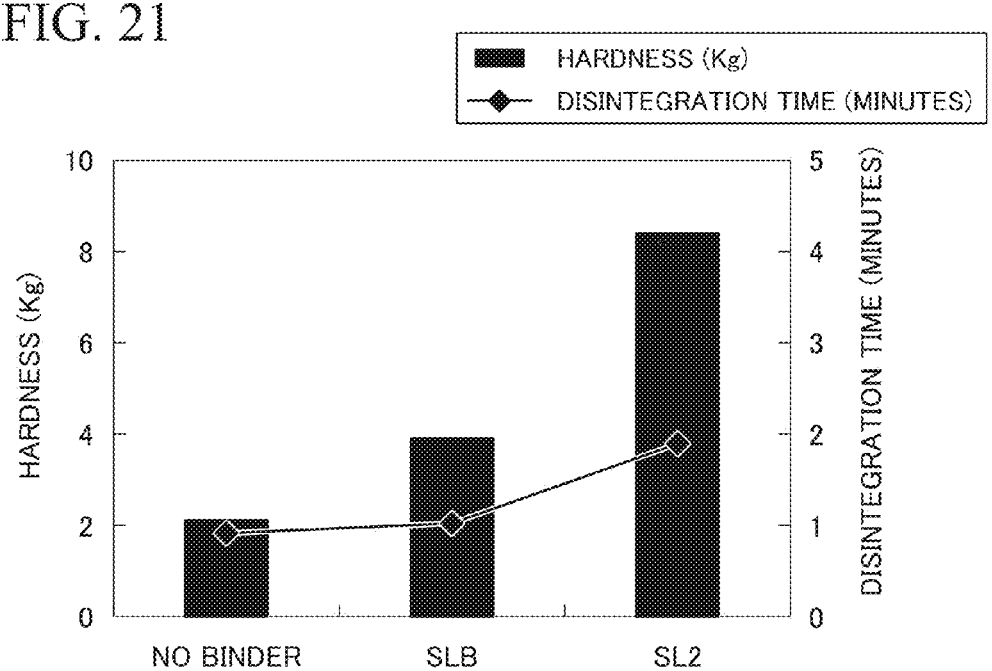
FIG. 21 is a diagram illustrating the hardness and disintegration time of tablets containing acetaminophen, lactose and corn starch obtained in Example 8 and Comparative example 4.

5% by weight of a hydroxypropylcellulose, 50% by weight of acetaminophen (fine powder, manufactured by Yamamoto Corporation), 31.5% by weight of lactose (Dailactose S, manufactured by Freund Corporation), 13.5% by weight of a corn starch (Corn Starch W, manufactured by Nihon Shokuhin Kako Co., Ltd.) and 0.5% by weight of magnesium stearate (in outer percentage) were mixed together thoroughly to obtain a preparation E. With the exception of using the preparation E, a tablet E was obtained using the same procedure as that described above for the tablet A. For the tablet E, the tablet hardness and disintegration time were determined using the same procedures as described above. These results are shown in FIG. 21.

For the hydroxypropylcellulose, hydroxypropylcellulose microparticles SL2 having a volume-average particle size of 13 μm obtained using the same procedure as that described for Example 2, and a hydroxypropylcellulose obtained by passing the hydroxypropylcellulose bulk powder HPC SL through a 100-mesh (hereinafter abbreviated as SLB, volume-average particle size: 40 μm) were used.

Comparative Example 4

50% by weight of acetaminophen (fine powder, manufactured by Yamamoto Corporation), 35% by weight of lactose (Dailactose S, manufactured by Freund Corporation), 15% by weight of a corn starch (Corn Starch W, manufactured by Nihon Shokuhin Kako Co., Ltd.) and 0.5% by weight of magnesium stearate (in outer percentage) were mixed together thoroughly to obtain a preparation F. With the exception of using the preparation F, a tablet F was obtained using the same procedure as that described above for the method of producing the tablet A. For the tablet F, the tablet hardness and disintegration time were determined using the same procedures as described above. These results for no binder are shown in FIG. 21.

Example 9

Figure 22:
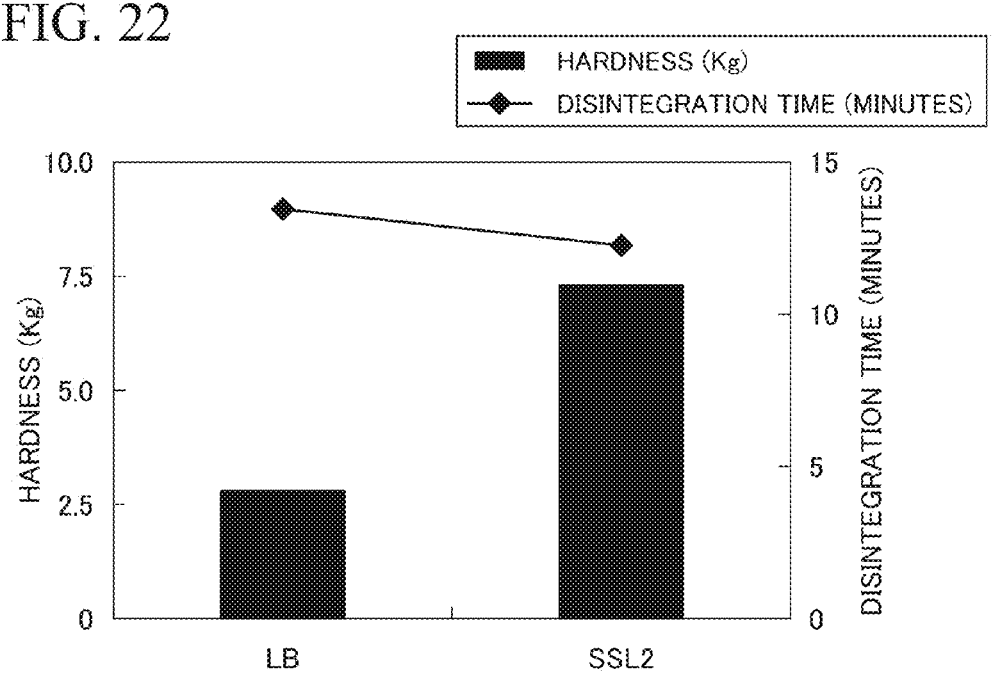
FIG. 22 is a diagram illustrating the hardness and disintegration time of tablets containing hydroxypropylcellulose microparticles, glucosamine and a sugar ester obtained in Example 9.

10% by weight of a hydroxypropylcellulose, 86% by weight of glucosamine (Glucosamine GM, manufactured by Protein Chemical Co., Ltd.) and 4% by weight of a sugar ester (S-370F, manufactured by Mitsubishi Chemical Corporation) were mixed together thoroughly to obtain a preparation G. With the exception of using the preparation G, a tablet G was obtained using the same procedure as that described above for the method of producing the tablet A. For the tablet G, the tablet hardness and disintegration time were determined using the same procedures as described above. These results are shown in FIG. 22.

For the hydroxypropylcellulose, the hydroxypropylcellulose LB obtained by passing the hydroxypropylcellulose bulk powder HPC L through a 100-mesh, and hydroxypropylcellulose microparticles SSL2 having a volume-average particle size of 12 nm obtained using the same procedure as that described for Example 4 were used.

Example 10

3 parts by weight of hydroxypropylcellulose microparticles SSL2 having a volume-average particle size of 12 μm obtained using the same procedure as that described for Example 4, 1 part by weight of magnesium stearate (lubricant), 1 part by weight of crospovidone (disintegrator) and 95 parts by weight of erythritol were subjected to tablet compression at a compression pressure of 200 MPa, yielding a tablet H. 3 parts by weight of SSL2, 3 parts by weight of a sucrose fatty acid ester (SE, S-170, manufactured by MITSUBISHIKAGAKU FOODS CORPORATION) (lubricant), 1 part by weight of crospovidone (disintegrator) and 93 parts by weight of erythritol were subjected to tablet compression at a compression pressure of 200 MPa, yielding a tablet I. 2 parts by weight of SSL2, 3 parts by weight of a sucrose fatty acid ester (SE, S-170, manufactured by MITSUBISHIKAGAKU FOODS CORPORATION) (lubricant), 1 part by weight of crospovidone (disintegrator) and 94 parts by weight of erythritol were subjected to tablet compression at a compression pressure of 200 MPa, yielding a tablet J. 1.5 parts by weight of SSL2, 3 parts by weight of a sucrose fatty acid ester (SE, S-170, manufactured by MITSUBISHIKAGAKU FOODS CORPORATION) (lubricant), 1 part by weight of crospovidone (disintegrator) and 94.5 parts by weight of erythritol were subjected to tablet compression at a compression pressure of 200 MPa, yielding a tablet K.

The tensile strength, disintegration time and intraoral disintegration time for the tablets H to K were as shown in Table 4. The "intraoral disintegration time" refers to the average time, across six male and female adults, determined by rinsing the mouth with distilled water, placing a tablet in the mouth, and measuring the time taken for the tablet to disintegrate completely without chewing.

The tensile strength decreased as the amount of hydroxypropylcellulose microparticles was reduced, but even for the formulation containing 1.5 parts by weight of the hydroxypropylcellulose microparticles (tablet K), a tensile strength of 1 MPa was obtained. The disintegration time was substantially the same for all of the formulations. Further, the intraoral disintegration time for the tablet K was approximately 20 seconds. These results confirmed that by using the hydroxypropylcellulose microparticles, tablets having excellent intraoral disintegration properties could be prepared.

TABLE 4

|  | Tensile strength (MPa) | Disintegration time (seconds) | Intraoral disintegration time (seconds) |
|---|---|---|---|
| Tablet H | 1.5 ± 0.1 | 18.8 ± 1.3 | 45.7 ± 4.6 |
| Tablet I | 1.5 ± 0.1 | 18.0 ± 0.8 | 36.5 ± 3.4 |
| Tablet J | 1.2 ± 0.1 | 17.8 ± 1.5 | 27.0 ± 4.8 |
| Tablet K | 1.0 ± 0.1 | 18.0 ± 1.4 | 21.8 ± 2.7 |

The invention claimed is:

1. A method of producing hydroxyalkylcellulose microparticles, the method comprising:
    generating a pulse shock wave, and supplying a hydroxyalkylcellulose aqueous solution to a pulse shock wave generation region, thereby crushing and drying the hydroxyalkylcellulose aqueous solution,
    wherein the hydroxyalkylcellulose supplied as the aqueous solution has a viscosity at 20° C. for a 2% aqueous solution that is within a range from 2.0 to 20.0 mPa·s.

2. The method of producing hydroxyalkylcellulose microparticles according to claim 1, wherein a concentration of the hydroxyalkylcellulose aqueous solution is within a range from 1 to 5% by weight.

3. The method of producing hydroxyalkylcellulose microparticles according to claim 1, wherein a shape of the obtained hydroxyalkylcellulose microparticles is spherical.

4. The method of producing hydroxyalkylcellulose microparticles according to claim 1, wherein the hydroxyalkylcellulose supplied as an aqueous solution has a hydroxyalkyl group content within a range from 40 to 80% by weight.

5. The method of producing hydroxyalkylcellulose microparticles according to claim 1, wherein the hydroxyalkylcellulose supplied as an aqueous solution is a hydroxypropylcellulose.

* * * * *

UNITED STATES PATENT AND TRADEMARK OFFICE
CERTIFICATE OF CORRECTION

PATENT NO. : 9,090,714 B2  
APPLICATION NO. : 14/021995  
DATED : July 28, 2015  
INVENTOR(S) : Takeuchi et al.

It is certified that error appears in the above-identified patent and that said Letters Patent is hereby corrected as shown below:

On the Title page of the patent, please replace Item (71) with the following:

-- (71) Applicants: Hirofumi Takeuchi, Gifu (JP); Satoru Abe, Joetsu (JP); Takeshi Shimotori, Myoko (JP); Gentaro Nemoto, Yamato (JP) --

Signed and Sealed this
Ninth Day of February, 2016

Michelle K. Lee
*Director of the United States Patent and Trademark Office*